US010188448B2

(12) United States Patent
Friedrichs

(10) Patent No.: US 10,188,448 B2
(45) Date of Patent: Jan. 29, 2019

(54) ELECTROSURGICAL SYSTEM FOR MULTI-FREQUENCY INTERROGATION OF PARASITIC PARAMETERS OF AN ELECTROSURGICAL INSTRUMENT

(71) Applicant: COVIDIEN LP, Mansfield, MA (US)

(72) Inventor: Daniel A. Friedrichs, Aurora, CO (US)

(73) Assignee: COVIDIEN LP, Mansfield, MA (US)

( * ) Notice: Subject to any disclaimer, the term of this patent is extended or adjusted under 35 U.S.C. 154(b) by 637 days.

(21) Appl. No.: 14/877,079

(22) Filed: Oct. 7, 2015

(65) Prior Publication Data

US 2016/0143685 A1 May 26, 2016

Related U.S. Application Data

(60) Provisional application No. 62/082,691, filed on Nov. 21, 2014.

(51) Int. Cl.
*A61B 18/12* (2006.01)
*A61B 18/00* (2006.01)
(Continued)

(52) U.S. Cl.
CPC ...... *A61B 18/1206* (2013.01); *A61B 18/1233* (2013.01); *A61B 18/1402* (2013.01);
(Continued)

(58) Field of Classification Search
CPC . A61B 18/1206; A61B 18/1233; A61B 18/16; A61B 2018/128;
(Continued)

(56) References Cited

U.S. PATENT DOCUMENTS 5,743,900 A 4/1998 Hara
5,843,021 A 12/1998 Edwards et al.
(Continued)

FOREIGN PATENT DOCUMENTS

CN 101862219 A 10/2010
CN 103260539 A 8/2013
(Continued)

OTHER PUBLICATIONS

Chinese Office Action dated Sep. 20, 2017 in correpsonding Chinese Patent Application No. 201510698667.8 together with English translation, 19 pages.
(Continued)

*Primary Examiner* — Thomas Giuliani

(57) ABSTRACT

An electrosurgical system includes an electrosurgical generator and an instrument coupled to the electrosurgical generator. The electrosurgical generator includes an output stage configured to generate the electrosurgical energy at a plurality of radio frequencies, a plurality of sensors configured to sense a voltage waveform and a current waveform of the electrosurgical energy, and a controller coupled to the output stage and the plurality of sensors. The instrument supplies the electrosurgical energy to the tissue. The controller of the electrosurgical generator is further configured to calculate at least one parasitic parameter based on the electrosurgical energy at the plurality of frequencies and control the output stage based on the at least one parasitic parameter.

9 Claims, 5 Drawing Sheets

(51) Int. Cl.
*A61B 18/14* (2006.01)
*A61B 18/16* (2006.01)

(52) U.S. Cl.
CPC ........... *A61B 18/1445* (2013.01); *A61B 18/16* (2013.01); *A61B 2018/00178* (2013.01); *A61B 2018/00648* (2013.01); *A61B 2018/00702* (2013.01); *A61B 2018/00827* (2013.01); *A61B 2018/00875* (2013.01); *A61B 2018/00892* (2013.01); *A61B 2018/00988* (2013.01); *A61B 2018/128* (2013.01)

(58) Field of Classification Search
CPC ........... A61B 2018/00827; A61B 2018/00875; A61B 2018/00892; A61B 2018/00648; A61B 2018/00642; A61B 2018/00702; A61B 2018/00178; A61B 2018/00988
USPC ............................................................ 606/34
See application file for complete search history.

(56) References Cited

U.S. PATENT DOCUMENTS

| | | | |
|---|---|---|---|
| 6,019,757 A | 2/2000 | Scheldrup | |
| 6,171,304 B1 | 1/2001 | Netherly | |
| D574,323 S | 8/2008 | Waaler | |
| 7,736,358 B2 | 6/2010 | Shores et al. | |
| 7,799,020 B2 | 9/2010 | Shores et al. | |
| 8,298,223 B2 | 10/2012 | Wham et al. | |
| 8,753,334 B2 | 6/2014 | Behnke et al. | |
| 2005/0113819 A1 | 5/2005 | Wham et al. | |
| 2006/0224152 A1 | 10/2006 | Behnke et al. | |
| 2007/0173804 A1 | 7/2007 | Wham et al. | |
| 2009/0018536 A1 | 1/2009 | Behnke | |
| 2009/0048595 A1* | 2/2009 | Mihori | A61B 18/1206 606/49 |
| 2009/0157067 A1 | 6/2009 | Kane et al. | |
| 2009/0234353 A1 | 9/2009 | McPherson | |
| 2009/0237042 A1 | 9/2009 | Glovinski | |
| 2010/0121318 A1 | 5/2010 | Hancock et al. | |
| 2011/0112526 A1 | 5/2011 | Fritz et al. | |
| 2011/0144635 A1 | 6/2011 | Harper et al. | |
| 2012/0265195 A1 | 10/2012 | Gilbert | |
| 2013/0066238 A1 | 3/2013 | Irisawa et al. | |
| 2014/0180274 A1* | 6/2014 | Kabaya | A61B 17/320092 606/34 |
| 2014/0232463 A1 | 8/2014 | Gilbert | |
| 2014/0243815 A1 | 8/2014 | Kerr | |
| 2014/0253140 A1 | 9/2014 | Gilbert | |
| 2014/0254221 A1 | 9/2014 | Johnson et al. | |
| 2014/0257270 A1 | 9/2014 | Behnke | |
| 2014/0258800 A1 | 9/2014 | Gilbert | |
| 2014/0276749 A1 | 9/2014 | Johnson | |
| 2014/0276750 A1 | 9/2014 | Gilbert | |
| 2014/0276753 A1 | 9/2014 | Wham et al. | |
| 2014/0276754 A1 | 9/2014 | Gilbert et al. | |
| 2014/0358138 A1 | 12/2014 | Mattmiller et al. | |
| 2014/0376269 A1 | 12/2014 | Johnson et al. | |
| 2015/0025521 A1 | 1/2015 | Friedrichs et al. | |
| 2015/0025523 A1 | 1/2015 | Friedrichs et al. | |
| 2015/0032096 A1 | 1/2015 | Johnson | |
| 2015/0032098 A1 | 1/2015 | Larson et al. | |
| 2015/0032099 A1 | 1/2015 | Larson et al. | |
| 2015/0032100 A1 | 1/2015 | Coulson et al. | |
| 2015/0088116 A1 | 3/2015 | Wham | |
| 2015/0088124 A1 | 3/2015 | Wham | |
| 2015/0088125 A1 | 3/2015 | Wham | |
| 2015/0119871 A1 | 4/2015 | Johnson et al. | |

FOREIGN PATENT DOCUMENTS

| | | |
|---|---|---|
| DE | 179607 C | 3/1905 |
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1366724 A1 | 12/2003 |
| EP | 1707144 A1 | 10/2006 |
| EP | 1776929 A1 | 4/2007 |
| EP | 2301463 A1 | 3/2011 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| JP | 63 005876 A | 1/1988 |
| JP | 2002-065690 A | 3/2002 |
| JP | 2005-185657 A | 7/2005 |
| SU | 166452 | 1/1965 |
| SU | 727201 A2 | 4/1980 |
| WO | 02/11634 A1 | 2/2002 |
| WO | 02/45589 A2 | 6/2002 |
| WO | 03/090635 A1 | 11/2003 |
| WO | 06/050888 A1 | 5/2006 |
| WO | 08/053532 A1 | 5/2008 |
| WO | 2008063195 A1 | 5/2008 |
| WO | 2011126580 A2 | 10/2011 |

OTHER PUBLICATIONS

Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.

(56) References Cited

OTHER PUBLICATIONS

Muller et al. "Extended Left Hemicolectomy Using the LigaSure Vessel Sealing System", Innovations That Work; Company Newsletter; Sep. 1999.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance", Applied Neurophysiology 51:(1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.
Chicharo et al. "A Sliding Goertzel Algoritn" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
European Search Report dated Jun. 10, 2016 in corresponding European Patent Application No. EP15191314.

\* cited by examiner

ELECTROSURGICAL SYSTEM FOR MULTI-FREQUENCY INTERROGATION OF PARASITIC PARAMETERS OF AN ELECTROSURGICAL INSTRUMENT

CROSS REFERENCE TO RELATED APPLICATION

The present application claims the benefit of and priority to U.S. Provisional Application Ser. No. 62/082,691, filed on Nov. 21, 2014, the entire contents of which are incorporated herein by reference.

BACKGROUND

1. Technical Field

The present disclosure relates to an electrosurgical system for interrogating parasitic parameters of an electrosurgical instrument. More particularly, the present disclosure relates to systems and methods for interrogating parasitic parameter of an electrosurgical instrument that relays electrosurgical energy to tissue based on interrogation using electrosurgical energy at multi-frequencies.

2. Background of Related Art

An electrosurgical generator makes use of voltage and current sensors to measure quantities, such as power, for controlling the output of the electrosurgical generator to achieve a desired clinical effect. A cable, which may be more than a meter in length, and an electrosurgical instrument connect the electrosurgical generator to the active and return electrodes and are used to deliver electrosurgical energy to tissue being treated. The cable and the electrosurgical instrument create a circuit network between the voltage and current sensors and the tissue being treated and distort the voltage and current waveforms generated by the electrosurgical generator so that the voltage and current waveforms deviate from the desired sinusoidal, rectangular, sawtooth, pulse, triangular, or blended waveforms commonly used for electrosurgery.

Some cables and/or electrosurgical instruments have identifiers storing previously measured parasitic parameters, which may be recognized by an electrosurgical system. Stored information may include capacitance and inductance values of the cable and the electrosurgical instrument. However, the information contained in the identifier stores information of average values of a same kind but does not hold information specific to each cable and electrosurgical instrument. Thus, in a case where the cable or the electrosurgical instrument is an outlier, the information contained in the identifier may be resulting in inaccurate measurement of the supplied electrosurgical energy. During use, parasitic parameters of the cable and the electrosurgical instrument change due to the topology of the cable and the frequency of the electrosurgical energy. Thus, the information contained in the identifier may not be valid during the electrosurgery.

Thus, to more accurately monitor power, the parasitic parameters of the cable, and the electrosurgical instrument, these components need to be interrogated to accurately control the magnitude of the electrosurgical energy during electrosurgery to obtain desired surgical effects.

SUMMARY

The systems and methods of the present disclosure interrogate parasitic parameters of a cable and an electrosurgical instrument that relay electrosurgical energy to a target tissue. In the case of electrosurgery, the level of power supplied to the tissue may be controlled based on control parameters, which are based on the interrogated parasitic parameters.

An electrosurgical system includes an electrosurgical generator and an instrument coupled to the electrosurgical generator. The electrosurgical generator includes an output stage configured to generate the electrosurgical energy at a plurality of radio frequencies, a plurality of sensors configured to sense a voltage waveform and a current waveform of the electrosurgical energy, and a controller coupled to the output stage and the plurality of sensors. The instrument supplies the electrosurgical energy to the tissue. The controller of the electrosurgical generator is further configured to calculate at least one parasitic parameter based on the electrosurgical energy at the plurality of frequencies and control the output stage based on the at least one parasitic parameter.

In an aspect, the electrosurgical system further includes a cable serially coupling the instrument to the electrosurgical generator. The at least one parasitic parameter includes an inductive impedance and a capacitive impedance of the cable, and includes a capacitive impedance of the instrument. The capacitive impedance of the cable and the capacitive impedance of the instrument are connected in parallel.

In another aspect, the controller is further configured to calculate an output impedance at each of the plurality of radio frequencies based on the sensed voltage and current waveforms. The controller is further configured to calculate the parasitic parameters of the cable and the instrument based on an output impedance of each of the plurality of radio frequencies.

In a further aspect, a number of the plurality of radio frequencies is based on a number of the parasitic parameters.

In yet another aspect, the controller calculates the parasitic parameters before or during transmission of the electrosurgical energy to the instrument. The output stage is a non-resonant inverter.

In another embodiment, a method for controlling amplitude of electrosurgical energy includes generating at an electrosurgical generator electrosurgical energy at a plurality of radio frequencies, transmitting electrosurgical energy to an instrument coupled to the electrosurgical generator through a cable, sensing voltage and current of the electrosurgical energy, calculating an output impedance based on the sensed voltage and current waveforms at each of the plurality of frequencies, calculating at least one parasitic parameter of the cable and the instrument based on the output impedances, controlling amplitude of the electrosurgical energy based on the at least one parasitic parameter, and calculating an impedance of the tissue based on the parasitic parameters.

In an aspect, a cable serially couples the instrument to the electrosurgical generator. The at least one parasitic parameter includes an inductive impedance and a capacitive impedance of the cable. The at least one parasitic parameter includes a capacitive impedance of the instrument.

In another aspect, a capacitor of the cable and a capacitor of the instrument are connected in parallel. Calculating an impedance of the tissue includes calculating a voltage across the instrument based on the sensed current and the sensed voltage, and calculating a leakage current passing through the capacitor of the cable based on the voltage across the instrument. Calculating an impedance of the tissue further includes calculating a voltage across the tissue based on the leakage current passing through the capacitor of the instrument and the sensed current, and calculating a leakage current passing through the capacitor of the instrument based on the voltage across the tissue and a capacitive impedance of the instrument.

In yet another aspect, the method further includes calculating a current passing through the tissue based on the voltage across the tissue and the leakage current, and determining the impedance of the tissue based on current passing through the tissue and the voltage across the tissue.

In a further aspect, a number of the plurality of radio frequencies is based on a number of the at least one parasitic parameter.

In yet another embodiment, a non-transitory computer-readable medium storing instructions that, when executed by a processor, perform a method for controlling amplitude of electrosurgical energy generated by an electrosurgical generator to treat tissue via a cable and an instrument, the method includes generating at an electrosurgical generator electrosurgical energy at a plurality of radio frequencies, transmitting electrosurgical energy to an instrument coupled to the electrosurgical generator through a cable, sensing voltage and current of the electrosurgical energy, calculating an output impedance based on the sensed voltage and current waveforms at each of the plurality of frequencies, calculating at least one parasitic parameter of the cable and the instrument based on the output impedances, controlling amplitude of the electrosurgical energy based on the at least one parasitic parameter, and calculating an impedance of the tissue based on the parasitic parameters.

Any of the above aspects and embodiments of the present disclosure may be combined without departing from the scope of the present disclosure.

BRIEF DESCRIPTION OF THE DRAWINGS

Various embodiments of the present disclosure are described with reference to the accompanying drawings wherein.

DETAILED DESCRIPTION

During use of an electrosurgical system it is desirable to determine the parasitic parameters of a cable and an electrosurgical instrument, which relay electrosurgical energy to tissue, to provide an appropriate control over electrosurgical energy applied to a target tissue. Parasitic parameters distort the electrosurgical energy delivered to the tissue. The present disclosure provides for an electrosurgical generator configured to determine parasitic parameters of the cable, the instrument, and other components interconnecting the generator to the patient using electrosurgical energy supplied thereto at multiple frequencies. The electrosurgical generator thereafter determines control parameters to compensate for various parasitic parameters based on the frequency sweep of the connected components.

Figure 1:
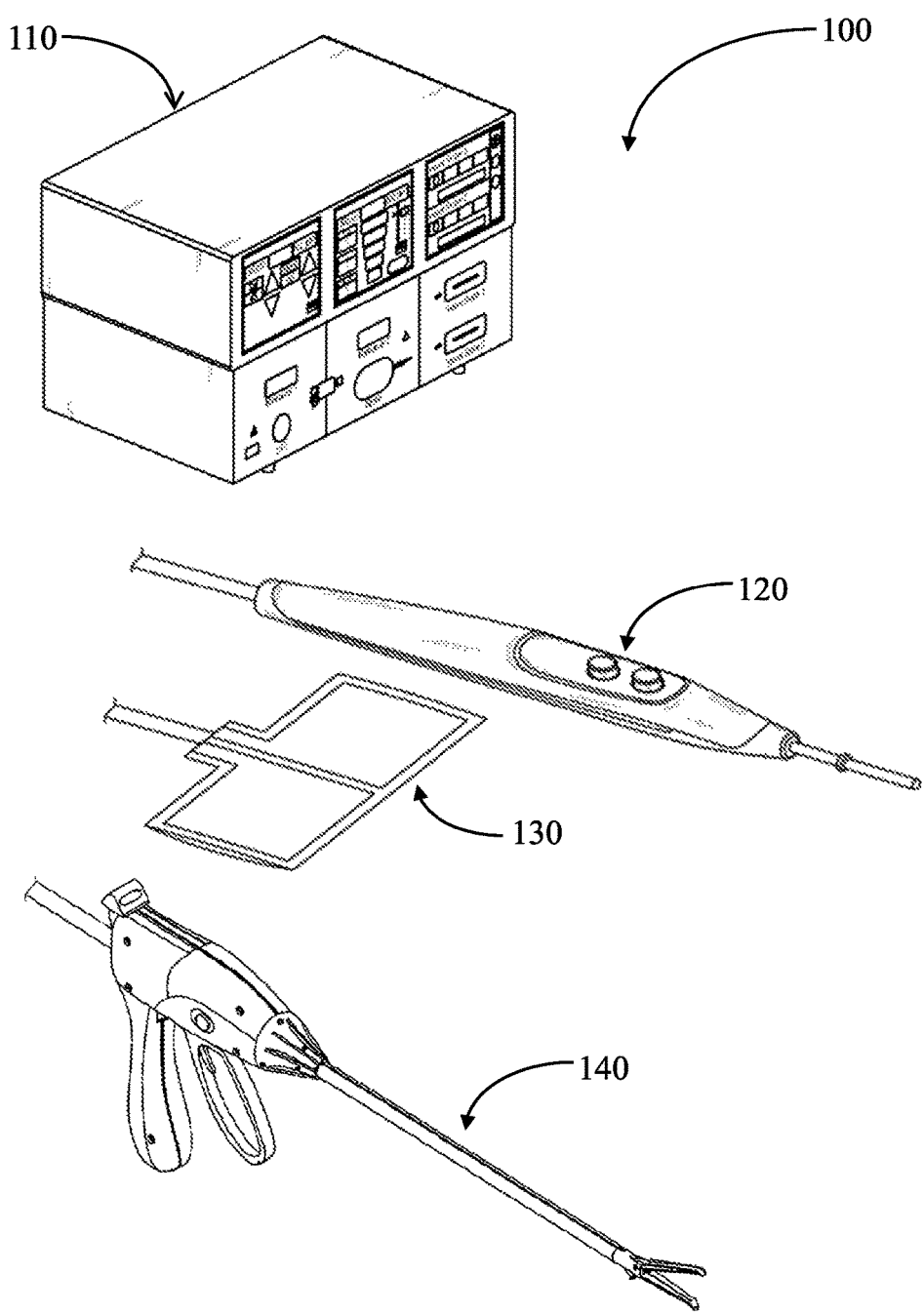
FIG. 1 is a perspective view of an electrosurgical system in accordance with embodiments of the present disclosure.

FIG. 1 illustrates an electrosurgical system 100 in accordance with embodiments of the present disclosure. The electrosurgical system 100 includes an electrosurgical generator 110 which generates electrosurgical energy for treating tissue of a patient. The electrosurgical generator 110 generates electrosurgical energy having appropriate amplitude based on the selected mode of operation (e.g., cutting, coagulating, ablating, or sealing), the voltage and current waveforms of the electrosurgical energy, and combinations thereof. The electrosurgical generator 110 may also include a plurality of output connectors for coupling the electrosurgical generator 110 with a variety of electrosurgical instruments.

The electrosurgical system 100 may include a monopolar electrosurgical instrument 120 having an electrode for treating tissue of the patient (e.g., an electrosurgical cutting probe, also known as an electrosurgical pencil, or an ablation electrode) with a return pad 130. The monopolar electrosurgical instrument 120 can be connected to the electrosurgical generator 110 via one of the plurality of output connectors. The electrosurgical energy is supplied to the monopolar electrosurgical instrument 120, which applies the electrosurgical energy to treat the tissue. The electrosurgical energy is returned to the electrosurgical generator 110 through the return pad 130. The return pad 130 provides a sufficient contact area with the patient's tissue so as to minimize the density of the current passing through the return pad 130 and to minimize the risk of tissue damage.

The electrosurgical system 100 may also include a bipolar electrosurgical instrument 140 including a pair of opposing jaw member. The bipolar electrosurgical instrument 140 can be connected to the electrosurgical generator 110 via one of the plurality of output connectors. The electrosurgical energy is supplied to one of the two jaw members, is applied to treat the tissue, and is returned to the electrosurgical generator 110 through the other jaw member.

As noted above, the electrosurgical generator 110 may also be configured to operate in a variety of modes, such as ablation, cutting, coagulation, and sealing. The electrosurgical generator 110 may include a switching mechanism (e.g., relays) to switch the supply of RF energy among the connectors to which various electrosurgical instruments may be connected. In embodiments, the electrosurgical generator 110 may be configured to provide RF energy to a plurality instruments simultaneously.

In further embodiments, the electrosurgical generator 110 may include a user interface having suitable user controls (e.g., buttons, activators, switches, or touch screens) for providing control parameters to the electrosurgical generator 110. These controls allow the user to adjust parameters of the electrosurgical energy (e.g., the power amplitude or the shape of the output waveform) so that the electrosurgical energy is suitable for a particular surgical mode (e.g., coagulating, ablating, tissue sealing, or cutting). The electrosurgical instruments 120 and 140 may also include a plurality of user controls. In addition, the electrosurgical generator 110 may include one or more display screens for displaying a variety of information related to operation of the electrosurgical generator 110 (e.g., intensity settings and treatment complete indicators).

In embodiments, the electrosurgical generator 110 may generate electrosurgical energy having a separate frequency based on the mode or progress of electrosurgery. In further embodiments, the electro surgical generator 110 may generate RF energy having a plurality of radio frequencies.

Figure 2:
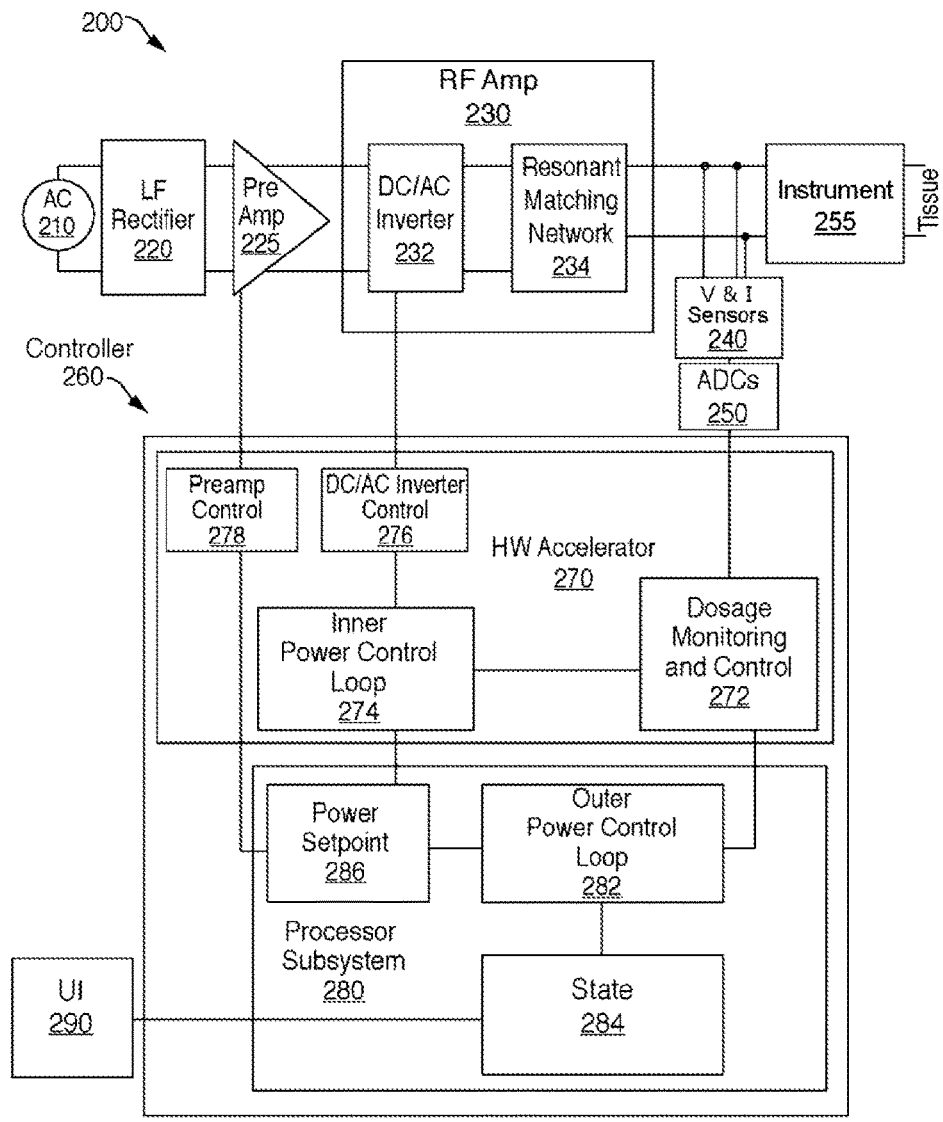
FIG. 2 is a block diagram of a generator circuitry of the electrosurgical generator of FIG. 1 and an instrument connected to the generator circuitry in accordance with embodiments of the present disclosure.

FIG. 2 is a block diagram of generator circuitry 200 of the electrosurgical generator 110 of FIG. 1 and an electrosurgical instrument 255 connected to the generator circuitry 200 via a cable. The generator circuitry 200 includes a low frequency (LF) rectifier 220, a preamplifier 225, an RF amplifier 230, a plurality of sensors 240, analog-to-digital converters (ADCs) 250, a controller 260, and a user interface (UI) 290. The electrosurgical generator 110 by way of the generator circuitry 200 connects to an alternating current (AC) power source 210, such as a wall power outlet or other power outlet, which generates AC power having a low frequency (e.g., 25 Hz, 50 Hz, or 60 Hz). The AC power source 210 provides AC power to the LF rectifier 220, which converts the AC to direct current (DC) power.

The DC output from the LF rectifier 220 is provided to the preamplifier 225, which amplifies the DC to a desired magnitude. The amplified DC is provided to the RF amplifier 230, which includes a direct current-to-alternating current (DC/AC) inverter 232 and an optional resonant matching network 234. The DC/AC inverter 232 inverts the amplified DC to an AC waveform having a frequency suitable for an electrosurgical procedure. In embodiments, the DC/AC inverter 232 may invert the amplified DC to an AC waveform including a plurality of frequencies, which may be used for interrogating the parasitic parameters of the cable and the instrument 255 and for treating target tissues.

The generator circuitry 200 may include a plurality of DC/AC inverters 232 to generate AC waveforms having different frequencies at the same time, which may be combined so that the combined electrosurgical energy has a plurality of frequencies. The present disclosure is not limited to the LF rectifier 220, the preamplifier 225, and the DC/AC inverter 232 to convert AC power having a low frequency to AC power having a plurality of frequencies but may employ any other suitable electrical components as can be appreciated by a person of ordinary skill in the art.

The appropriate frequency for the electrosurgical energy may differ based on electrosurgical procedures and modes of electrosurgery. For example, nerve and muscle stimulations cease at about 100,000 cycles per second (100 kHz) above which point some electrosurgical procedures can be performed safely allowing the electrosurgical energy to pass through a patient to targeted tissue with minimal neuromuscular stimulation. In embodiments, ablation procedures may use a frequency of 472 kHz. Other electrosurgical procedures may be performed at frequencies lower than 100 kHz, e.g., 29.5 kHz or 19.7 kHz, with minimal risk of damaging nerves and muscles. The DC/AC inverter 232 is also configured to output AC signals with various frequencies suitable for electrosurgical operations.

As described above, the RF amplifier 230 includes an optional resonant matching network 234. The optional resonant matching network 234 is coupled to the output of the DC/AC inverter 232 to match the impedance at the DC/AC inverter 232 to the impedance of the tissue so that there is maximum or optimal power transfer between the generator circuitry 200 and the tissue. In embodiments, a non-resonant inverter may be used for the DC/AC inverter 232 and the optional resonant matching network 234.

In an embodiment, a battery may directly provide DC power to the RF amplifier 230. In this situation, the AC power source 210, the LF rectifier 225, and the preamplifier 225 may be substituted with a buck converter, which amplifies the DC power from the battery to an appropriate level. Further, the battery makes the electrosurgical generator portable.

The plurality of sensors 240 sense voltage and current at the output of the RF amplifier 230. The plurality of sensors 240 may include two or more pairs or sets of voltage and current sensors that provide redundant measurements of the voltage and current waveforms. This redundancy ensures the reliability, accuracy, and stability of the voltage and current measurements at the output of the RF amplifier 230. In embodiments, the plurality of sensors 240 may include fewer or more sets of voltage and current sensors depending on the application or the design requirements. The plurality of sensors 240 may measure the voltage and current output at the output of the RF amplifier 230 and from other components of the generator circuitry 200 such as the DC/AC inverter 232 or the optional resonant matching network 234. The plurality of sensors 240 that measure the voltage and current may include any known technology for measuring voltage and current including, for example, a Rogowski coil.

The RF amplifier 230 is electrically coupled to the instrument 255 which may be the monopolar instrument 120, which has an antenna to emit electromagnetic waveforms, or the bipolar electrosurgical instrument 140 of FIG. 1, which has two jaw members to grasp and treat tissue with the energy provided by the RF amplifier 230.

The sensed voltage and current waveforms are fed into analog-to-digital converters (ADCs) 250. The ADCs 250 sample the sensed voltage and current waveforms to obtain digital samples of the voltage and current waveforms of the RF amplifier 230. The digital samples are processed by the controller 260 and used to generate a control signal to control the DC/AC inverter 232 of the RF amplifier 230 and the preamplifier 225. The ADCs 250 may be configured to sample outputs of the plurality of sensors 240 at a sampling frequency that is an integer multiple of the RF frequency.

As shown in FIG. 2, the controller 260 includes a hardware accelerator 270 and a processor subsystem 280. As described above, the controller 260 is also coupled to the UI 290, which receives input commands from a user and displays output and input information related to characteristics of the electrosurgical energy (e.g., selected power level). The hardware accelerator 270 processes the outputs from the ADCs 250 and cooperates with the processor subsystem 280 to generate control signals.

The hardware accelerator 270 includes a dosage monitoring and control (DMAC) 272, an inner power control loop 274, a DC/AC inverter controller 276, and a preamplifier controller 278. All or a portion of the controller 260 may be implemented by a field programmable gate array (FPGA), an application specific integrated circuit (ASIC), a digital signal processor (DSP), a microcontroller, and/or any other suitable logic circuit.

The DMAC 272 receives and processes digital samples of the sensed voltage and current waveforms to determine parasitic parameters and generate control parameters to the inner power control loop 274 based on the parasitic parameters. The parasitic parameter may include inductive and capacitive impedances of the cable and the electrosurgical instrument 255, and the control parameters may include a load current passing through a load (e.g., target tissue), a load voltage across the load, an average power delivered to the load, a load impedance (e.g., a real part of the tissue impedance) and/or a phase difference between the load current and the load voltage. The inner power control loop 274 may use one or more of the control parameters to send a control signal to the DC/AC inverter controller 276. The DC/AC inverter controller 276 in turn generates a first pulse-width modulation (PWM) control signal to control the output of the DC/AC inverter 232.

In an embodiment, the DMAC 272 may interrogate the parasitic parameters multiple times prior to or during application of electrosurgical energy. Newly interrogated parasitic parameters are compared with the previously interrogated parasitic parameters. When the difference between them is greater than a predetermined threshold stored in memory (not shown) associated with the DMAC 272, this indicates that the electrosurgical instrument 255 is being overused or not working properly. In response to exceeding the threshold, the DMAC 272 may issue an alarm, e.g., audio and/or visual, and/or immediately stop generating electrosurgical energy to prevent potential harm to the target tissue. Further, the DMAC 272 may preemptively disable the electrosurgical instrument 255.

The processor subsystem 280 also includes an outer power control loop 282, a state machine 284, and a power setpoint circuit 286. The processor subsystem 280 provides control signals for a second PWM control signal based on the output of the DMAC 272 and parameters (e.g., electrosurgical mode) selected by the user via the UI 290. Specifically, the parameters selected by the user are provided to the state machine 284 which determines a state or mode of the electrosurgery. The outer power control loop 282 uses this state information and the output (e.g., the control parameters) from the DMAC 272 to determine control information. The power setpoint circuit 286 receives the control information and generates and provides a power setpoint to the preamplifier controller 278, which, in turn, uses the power setpoint to generate a second PWM control signal for controlling the preamplifier 225 to amplify the DC output from the LF rectifier 220 to a desired magnitude. If the user does not provide operational parameters to the state machine 284 via the UI 290, then the state machine 284 may maintain or enter a default state.

Figure 3:
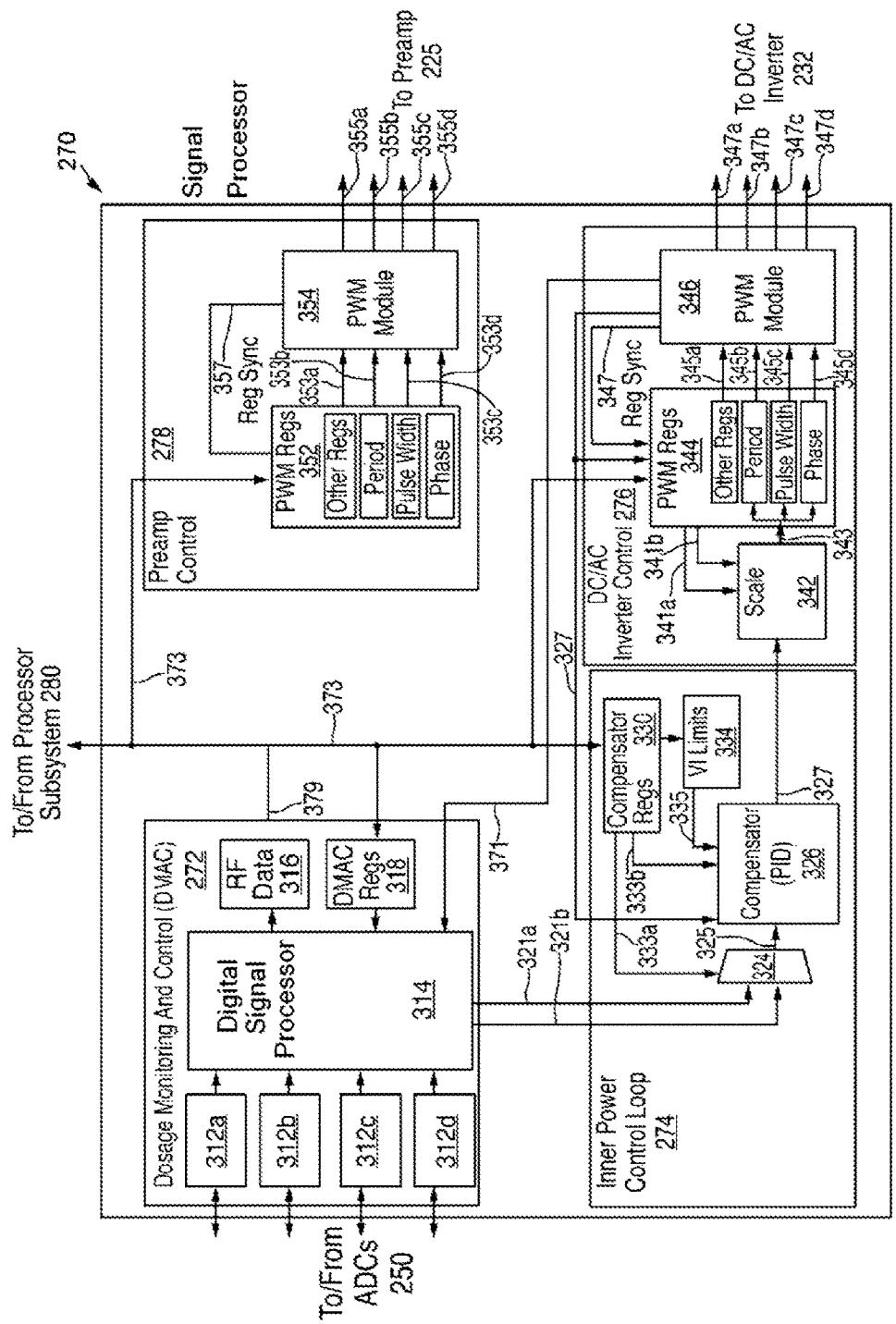
FIG. 3 is a functional block diagram of the controller of FIG. 2 in accordance with embodiments of the present disclosure.

FIG. 3 shows a more detailed functional diagram of the hardware accelerator 270 of FIG. 2. The hardware accelerator 270 implements those functions of the generator circuitry 200 that may have special processing requirements such as high processing speeds. The hardware accelerator 270 includes the DMAC 272, the inner power loop control 274, the DC/AC inverter controller 276, and the preamplifier controller 278.

The DMAC 272 includes a plurality of analog-to-digital converter (ADC) controllers 312a-312d, a digital signal processor 314, an RF data registers 316, and DMAC registers 318. The plurality of ADC controllers 312a-312d control the operation of the ADCs 250 and convert sensed voltage and current waveforms into digital data which is then provided to the DSP 314.

The sensed voltage and current waveforms are input to the ADCs 250, which sample the sensed voltage and current waveforms. The ADC controllers 312a-312d provide operational parameters, including a predetermined sampling rate, to the ADCs 250 so that the ADCs sample synchronously the voltage and current waveforms at a predetermined sampling rate, e.g., a predetermined number of digital samples per second, or predetermined sampling period. The ADC controllers 312a-312d may be configured to control the ADCs 250 so that the sampling period corresponds to an integer multiple of the RF frequency of the electrosurgical energy.

The digital data obtained by sampling the sensed voltage and current waveforms is provided to the DSP 314 via the ADC controllers 312a-312d. The DSP 314 may use the digital data to calculate a root mean square (RMS) voltage and current values and estimate parasitic parameters of the instrument 255 and a cable, such as a cable 440. The parasitic parameters may include inductive and capacitive impedance of the cable and instrument 255. Estimation process and derivation of relationship are described in detail below with respect to FIG. 4.

The DSP 314 calculates and outputs load voltage, load current, and power applied to the load (e.g., target tissue), impedance of the load, and/or a phase difference between the load voltage and the load current based on the estimated parasitic parameters. These outputs are control parameters to control the amplitude of the electrosurgical energy. These outputs of the DSP 314 are provided to the processor subsystem 280 via RF data registers 316 and a signal line 379. The DMAC 272 also includes DMAC registers 318 that store and update relevant parameters. The DSP 314 further receives signals from a PWM module 346 of the DC/AC inverter controller 276.

The DMAC 272 provides the control parameters to the inner power control loop 274 via signal lines 321a and 321b and to the processor subsystem 280 via signal line 379. The number of signal lines to the inner power control loop 274 is not limited to two but extends to a number necessary to transfer outputs of the DSP 314 based on the number of control parameters. The inner power control loop 274 includes a multiplexer 324, a compensator 326, compensator registers 330, and VI limiter 334.

The multiplexer 324 receives the control parameters output from the DSP 314 via signal lines 321a and 321b. The multiplexer 324 also receives a select control signal from the compensator registers 330 via a signal line 333a and selects one of the control parameters based on the select control signal. The selected control parameter is provided to the compensator 326.

When there is a user input, the processor subsystem 280 receives the user input and processes it with the control parameters output from the DSP 314 via the signal line 379. The processor subsystem 280 provides control signals via a compensator registers 330 to a VI limiter 334, which corresponds to the power setpoint circuit 286 in FIG. 2. The VI limiter 334 then provides a desired power profile (e.g., a minimum and a maximum limits of the power for a set electrosurgical mode or operation) based on the user input and the control parameters of the DSP 314, the compensator registers 330 also provide other control parameters to the compensator 326, and then the compensator 326 combines all control parameters from the compensator registers 330 and the VI limiter 334 to generate output to the DC/AC inverter controller 276 via signal line 327.

The DC/AC inverter controller 276 receives a control parameter and outputs control signals that drives the DC/AC inverter 232. The DC/AC inverter controller 276 includes a scale unit 342, PWM registers 344, and the PWM module 346. The scale unit 342 scales the output of the compensator registers 330 by multiplying and/or adding a number to the output. The scale unit 342 receives a number for multiplication and/or a number for addition from the PWM registers 344 via signal lines 341a and 341b. The PWM registers 344 store several relevant parameters to control the DC/AC inverter 232, e.g., a period, a pulse width, and a phase of the AC signal to be generated by the DC/AC inverter 232 and other related parameters. The PWM module 346 receives output from the PWM registers 344 and generates four control signals, 347a-347d, that control four transistors of the DC/AC inverter 232 of the RF amplifier 230 of FIG. 2. The PWM module 346 also synchronizes its information with the information in the PWM registers 344 via a register sync signal 347.

The PWM module 346 further provides control signals to the compensator 326 of the inner power control loop 274. The processor subsystem 280 provides control signals to the PWM module 346. In this way, the DC/AC inverter controller 276 can control the DC/AC inverter 232 of the RF amplifier 230 with integrated internal inputs, including processed results from the plurality of sensors by the DMAC 272, and external inputs, including processed results from the user input by the processor subsystem 280).

The processor subsystem 280 also sends the control signals to the preamplifier controller 278 via signal line 373. The preamplifier controller 278 processes the control signals and generates another control signal so that the preamplifier 225 amplifies direct current to a desired level suitable for being converted by the RF amplifier 230. The Preamplifier controller 278 includes PWM registers 352 and a PWM module 354. The PWM registers 352 receive outputs from the processor subsystem 280 vial signal link 373 and stores relevant parameters along with the PWM registers 344. The PWM module 354 also sends a register sync signal to the PWM registers 352 and generates four control signals, 355a-355d, that control four transistors of the preamplifier 225 in FIG. 2.

Figure 4:
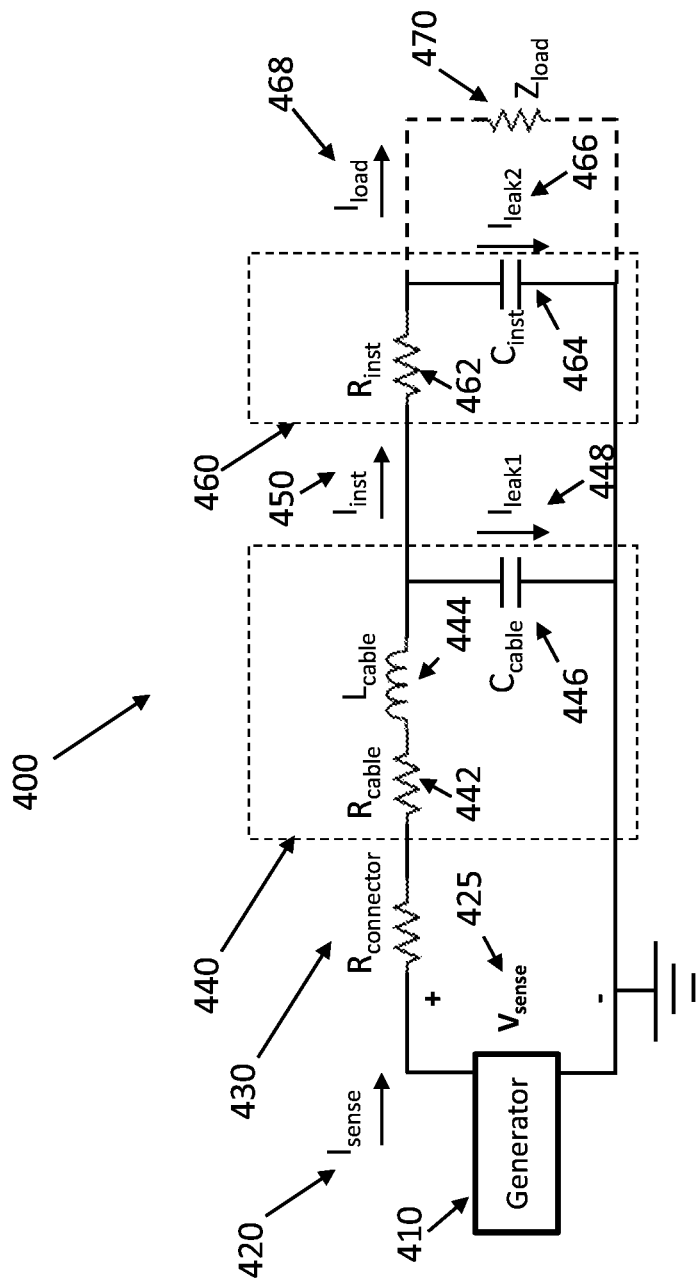
FIG. 4 is a circuit model of an electrosurgical system in accordance with embodiments of the present disclosure.

FIG. 4 shows a circuit model 400 of a cable 400 and an electrosurgical instrument 460 of an electrosurgical system in accordance with embodiments of the present disclosure. The circuit model 400 of an electrosurgical system includes an electrosurgical generator 410, a connector 430, the cable 440, and the electrosurgical instrument 460. The connector 430 connects the cable 440 with the electrosurgical generator 410 and has a resistive impedance 431 (i.e., $R_{connector}$).

The cable 440 is serially coupled with the electrosurgical generator 410 via the connector 430 at one end. The cable 440 is modeled as a resistor 442, an inductor 444, which is serially coupled with the resistor 442, and a capacitor 446, which is parallelly coupled with the inductor 444.

The electrosurgical instrument 460 is coupled to the other end of the cable 440 and is modeled as a resistor 462 and a capacitor 464. The resistor 462 of the electrosurgical instrument 460 is serially coupled with the cable 440 and the capacitor 464 of the electrosurgical instrument 460 is parallelly coupled with the capacitor 446 of the cable 440. The circuit model 400 is not limited to this configuration but may be further simplified or modified in any suitable manner as can be appreciated by a person of ordinary skill in the art.

Inductance of the inductor 444 of the cable 440 is $L_{cable}$, the capacitance of the capacitor 446 of the cable 440 is $C_{cable}$, and the capacitance of the capacitor 464 of the electrosurgical instrument is $C_{inst}$. Corresponding impedances of the inductor 444, the capacitor 446, and the capacitor 464, which represent parasitic impedances, may then be expressed as follows:

$$Z_L = 2\pi f L_{cable} j,$$

$$Z_{cable} = \frac{1}{2\pi f C_{cable} j}, \text{ and}$$

$$Z_{inst} = \frac{1}{2\pi f C_{inst} j},$$

respectively,
where f is a frequency of the electrosurgical energy passing through the circuit model 400.

As shown above, the capacitive impedances $Z_{cable}$ and $Z_{inst}$ of the cable 440 and the electrosurgical instrument 460, and the inductive impedance $Z_L$ of the cable 440 vary depending on a frequency of the electrosurgical energy. By estimating or interrogating these parasitic impedances or parasitic parameters including the capacitive impedances $Z_{cable}$ and $Z_{inst}$ and the inductive impedance $Z_L$, the load voltage $V_{load}$ across the load 470 and the load current $I_{load}$ passing through the load 470 can be determined. The parasitic parameters including the capacitive impedances $Z_{cable}$ and $Z_{inst}$ and the inductive impedance $Z_L$ may be estimated based on the current and voltage waveforms for each of the multiple frequencies of electrosurgical energy. The parasitic parameters may be sensed at the output of the electrosurgical generator 410 either prior to commencing electrosurgical treatment or during application of electrosurgical energy and with or without connecting the load 470 to the generator 410. Control parameters including the load voltage $V_{load}$, the load current $I_{load}$, the load impedance $Z_{load}$, the average power, and/or a phase difference between the load voltage $V_{load}$ and the load current $I_{load}$, may also be calculated based on the parasitic parameters. Calculations and derivation of the control parameters are detailed below.

After sensing the current and voltage waveforms, a current ($I_{sense}$) 420 and a voltage ($V_{sense}$) 425 are calculated. In an aspect, an RMS, a peak value, or mean value of the voltage or current may be used. An output impedance $Z_{out}$ may be calculated as follows:

$$Z_{out} = \frac{V_{sense}}{I_{sense}}.$$

The output impedance $Z_{out}$ seen from the electrosurgical generator 410 may be also expressed as follows:

$$Z_{out} = R_{connector} + R_{cable} + Z_L + \{Z_{cable}//(R_{inst}+Z_{inst})\},$$

where $R_{connector}$ is the resistive impedance of the connector, $R_{cable}$ is the resistive impedance of the cable 440, and $R_{inst}$ is the resistive impedance of the electrosurgical instrument 460. The notation "//" in $\{Z_{cable}//(R_{inst}+Z_{inst})\}$ shows a configuration in which the capacitor 446 of the cable 440 is coupled in parallel with the resistor 462 and the capacitor 464 of the electrosurgical instrument 460.

At the first frequency $f_1$, the output impedance $Z_{out1}$ may be expressed as follows:

$$Z_{out1} = R_{connector} + R_{cable} + 2\pi f_1 L_{cable} j + \left\{\frac{1}{2\pi f_1 C_{cable} j} // \left(R_{inst} + \frac{1}{2\pi f_1 C_{inst} j}\right)\right\} = R_{connector} + R_{cable} +$$

$$2\pi f_1 L_{cable} j + \frac{2\pi f_1 C_{inst} R_{inst} j + 1}{2\pi f_1 C_{cable} j(2\pi f_1 C_{inst} R_{inst} j + 1) + 2\pi f_1 C_{inst} j}.$$

In a case where the resistive impedance $R_{inst}$ of the instrument 460 is negligible, the output impedance $Z_{out1}$ may be simplified as follows:

$$Z_{out1} = R_{connector} + R_{cable} + 2\pi f_1 L_{cable} j + \frac{1}{2\pi f_1 (C_{cable} + C_{inst}) j}.$$

Similarly, at a second frequency $f_2$, the output impedance $Z_{out2}$ may be simplified as follows:

$$Z_{out2} = R_{connector} + R_{cable} + 2\pi f_2 L_{cable} j + \frac{1}{2\pi f_2 (C_{cable} + C_{inst})j}.$$

Based on a system of linear equations, the capacitive impedance ($C_{cable}+C_{inst}$) and the inductive impedance $L_{cable}$ may be expressed:

$$C_{cable} + C_{inst} = \frac{f_1^2 - f_2^2}{2\pi f_1 f_2 \left[ \begin{array}{c} f_2(Z_{out1} - R_{connector} - R_{cable}) - \\ f_1(Z_{out2} - R_{connector} - R_{cable}) \end{array} \right]} j \text{ and}$$

$$L_{cable} = \frac{f_2(Z_{out2} - R_{connector} - R_{cable}) - f_1(Z_{out1} - R_{connector} - R_{cable})}{2\pi(f_1^2 - f_2^2)} j.$$

In this way, the capacitive impedance and the inductive impedance may be calculated. In a case where the resistive impedance is not negligible, sensing voltage and current having another frequency different from the first and second frequencies may be used to calculate the parasitic impedances.

In an aspect, the parasitic parameters including the capacitive and inductive impedances may be interrogated during an electrosurgical operation to assure a certain level of accuracy to prevent damages to the target tissue.

In another aspect, multiple frequencies for interrogation of the parasitic parameters before an electrosurgical operation may be different from a multiple frequencies during the electrosurgical operation.

In still another aspect, the number of frequencies required for the interrogation may be dependent upon the number of the parasitic parameters.

After interrogating the parasitic parameters, the load impedance $Z_{load}$ of the load 470 (e.g., target tissue) may be calculated based on the parasitic parameters, current $I_{sense}$ 420, and voltage $V_{sense}$ 425 sensed by a plurality of sensors of the electrosurgical generator 410 when the load 470 is coupled with the electrosurgical instrument 460. The voltage $V_{cable}$ across the capacitor 446 may be determined as follows:

$$V_{cable} = V_{sensed} - I_{sense} \cdot (R_{connector} + R_{cable} + Z_L).$$

The sensed current $I_{sense}$ 420 is then divided into and runs through the capacitor 446 and the resistor 462. Relationship of currents is shown below:

$$I_{sense} = I_{leak1} + I_{inst},$$

where $I_{inst}$ is the current passing through the resistor 462. Further, the leakage current $I_{leak1}$ may be calculated by:

$$I_{leak1} = \frac{V_{cable}}{Z_{cable}},$$

where $Z_{cable}$ is the capacitive impedance of the capacitor 446. As a result, the current $I_{inst}$ is determined by:

$$I_{inst} = I_{sense} - \frac{V_{cable}}{Z_{cable}}.$$

The current $I_{inst}$ is also divided into another leakage current $I_{leak2}$ and current $I_{load}$ passing through the load 470. Relationship between currents is shown below:

$$I_{inst} = I_{leak2} + I_{load}.$$

The voltage across the capacitor 464 is the same as the load voltage $V_{load}$ across the load 470, which may be expressed by:

$$V_{load} = V_{cable} - I_{inst} \cdot R_{inst}.$$

Thus, the leakage current $I_{leak2}$ is calculated by:

$$I_{leak2} = \frac{V_{load}}{Z_{inst}}.$$

As a result, the load current $I_{load}$ and the load impedance $Z_{load}$ may be calculated by:

$$I_{load} = I_{inst} - I_{leak2}, \text{ and } Z_{load} = \frac{V_{load}}{I_{load}}.$$

This relationship allows for the determinations of the load current $I_{load}$ 468, the load voltage $V_{load}$, and the load impedance $Z_{load}$, which may then be used as control parameters to control the electrosurgical energy. A phase difference between the load voltage $V_{load}$ and the load current $I_{load}$ 468 and an average power may also be calculated.

The control parameters may be determined in real time during an electrosurgical operation. Further, based on these control parameters, including the load current $I_{load}$ 468 and the load voltage $V_{load}$, and the load impedance $Z_{load}$, the electrosurgical generator 410 may control the amplitude of the electrosurgical energy during the electrosurgical operation.

In embodiments, the capacitance and resistance of the electrosurgical instrument are negligibly small compared to the capacitance and the inductance of the cable. Thus, the output impedance $Z_{out}$ may be simplified and expressed by:

$$Z_{out} = R_{connector} + R_{cable} + Z_L + Z_{cable} =$$
$$R_{connector} + R_{cable} + 2\pi f L_{cable} j + \frac{1}{2\pi f C_{cable} j}.$$

Based on the similar calculations and derivations described above, the inductive impedance $L_{cable}$ of the inductor 444 may be expressed as follows:

$$L_{cable} = \frac{f_2(Z_{out2} - R_{connector} - R_{cable}) - f_1(Z_{out1} - R_{connector} - R_{cable})}{2\pi(f_1^2 - f_2^2)} j,$$

and
the capacitive impedance $C_{cable}$ of the capacitor 446 is:

$$C_{cable} = \frac{f_1^2 - f_2^2}{2\pi f_1 f_2 \left[ \begin{array}{c} f_2(Z_{out1} - R_{connector} - R_{cable}) - \\ f_1(Z_{out2} - R_{connector} - R_{cable}) \end{array} \right]} j.$$

Based on these parasitic parameters, the control parameters may also be determined in a similar manner as described above.

In embodiments, the resistive impedances $R_{connector}$ and $R_{inst}$ of the cable 440 and the connector 430 may be also negligible compared with the capacitive and inductive impedances. The parasitic parameters and the control parameters may be determined using computations and derivations described below. In embodiments, the capacitive and inductive impedances may be calculated as follows:

$$L_{cable} = \frac{f_2 Z_{out2} - f_1 Z_{out1}}{2\pi(f_1^2 - f_2^2)} j, \text{ and}$$

$$C_{cable} = \frac{f_1^2 - f_2^2}{2\pi f_1 f_2 (f_2 Z_{out1} - f_1 Z_{out2})} j.$$

In further embodiments, the capacitive and resistive impedances of the instrument 460, the cable 440, and the connector 430 may also be considered in determining parasitic parameters. The parasitic parameters may include the resistive impedance $R_{connector}$ of the connector 430, the resistive impedance $R_{cable}$, the inductive impedance $Z_L$ and the capacitive impedance $Z_{cable}$ of the cable 440, as well as the resistive impedance $R_{inst}$ and the capacitive impedance $Z_{inst}$ of the electrosurgical instrument 460. In this case, at least six different frequencies may be used to determine the parasitic parameters. In other words, the number of frequencies needed for determining the parasitic parameters depends on the number of the parasitic parameters.

In still further embodiments, the parasitic parameters may be re-interrogated during an electrosurgical operation to obtain further assurance of accuracy or to adjust the parasitic parameters due to changes in configuration of the cable or changes in temperature of the cable and/or the instrument. Re-interrogation may be performed when the electrosurgical instrument is not used during the electrosurgical operation.

Figure 5:
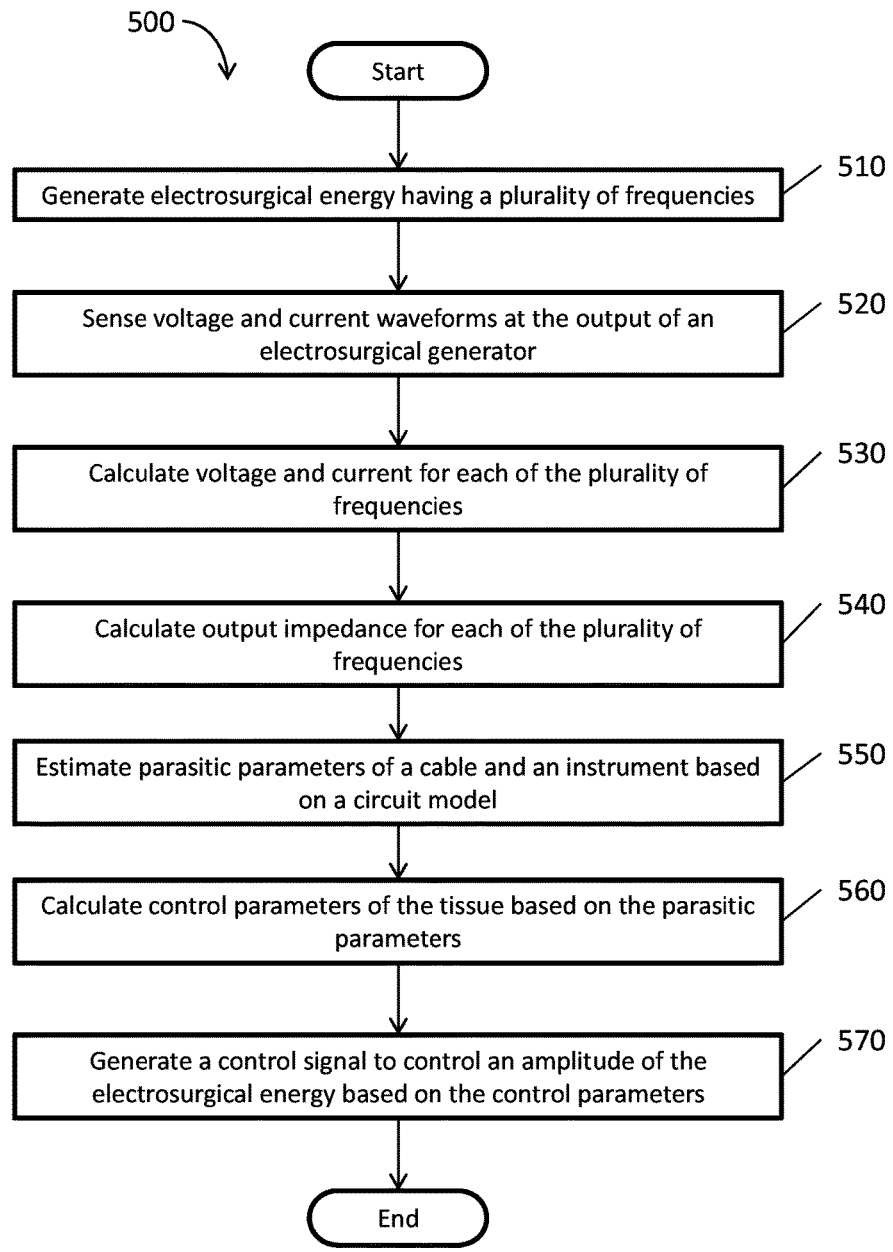
FIG. 5 is a flow diagram illustrating a method for interrogating parasitic parameters in accordance with embodiments of the present disclosure.

FIG. 5 shows a flow diagram illustrating a method 500 for controlling amplitude of the electrosurgical energy generated by an electrosurgical generator (e.g., 410 of FIG. 4) in accordance with embodiments of the present disclosure. The electrosurgical generator 410 may be serially coupled to the tissue 470 via the cable 440 and the electrosurgical instrument 460 as shown in FIG. 4. The method 500 starts by generating electrosurgical energy including a plurality of radio frequencies in step 510. The plurality of radio frequencies may be included in the electrosurgical energy. Each of the plurality of radio frequencies may be included in electrosurgical energy separately generated by the electrosurgical generator 410.

In step 520, the voltage and current waveforms of the electrosurgical energy are sensed by a plurality of sensors of the electrosurgical generator 410. The sensed voltage and current waveforms may be digitally sampled so that a root mean square (RMS) voltage and current may be calculated for each of the plurality of radio frequencies in step 530. In an aspect, an RMS, peak or mean value of the voltage and current waveforms may be calculated in step 530.

In step 540, based on the voltage and the current, output impedance is calculated for each of the plurality of radio frequencies by dividing the voltage by the current. In an aspect, an RMS, peak value, or mean value of the voltage or current may also be used to calculate the output impedance for each frequency in step 540. Based on a circuit model 400 of the cable 440 and the instrument 460, the parasitic parameters may be estimated using a system of equations described above based on the capacitive and inductive impedances of the cable 440 and the instrument 460 and with the output impedances.

In step 550, parasitic parameters of the cable 440 and the instrument 460 may be calculated from the system of equations. Once the parasitic parameters are calculated, current passing through and voltage across the corresponding electrical components of the circuit model 400 are analyzed and, control parameters are calculated in step 560. The control parameters may include load current $I_{load}$ 468 passing through the load 470 (e.g., target tissue), load voltage $V_{load}$ across the load 470, impedance of the load $Z_{load}$, average power applied to the load 470, and/or a phase difference between the load current $I_{load}$ 468 and the load voltage $V_{load}$.

In step 570, the control parameters are compared with an electrosurgical operational model for controlling and adjusting the amplitude of the electrosurgical energy. In an aspect, all of the control parameters may be compared or at least one of the control parameters may be compared to control the amplitude based on progress of the electrosurgical operation. For example, in the beginning stage of the electrosurgical operation, current may be a control parameter, power may be a control parameter in the intermediate stage, and voltage may be a control parameter at the end stage. In another aspect, this method 500 may be performed to determine the parasitic parameters before or during an electrosurgical operation.

In embodiments, the method 500 further includes comparing previously interrogated parasitic parameters with newly interrogated parasitic parameters, and determining whether the newly interrogated parasitic parameters are substantially different from the previously interrogated parasitic parameters. Substantial difference may indicate failure or over-usage of the electrosurgical instrument. In such cases of substantial differences, the method 500 further includes immediately stopping generation of electrosurgical energy and preemptively disabling the electrosurgical instrument.

Although the illustrative embodiments of the present disclosure have been described herein with reference to the accompanying drawings, it is to be understood that the disclosure is not limited to those precise embodiments, and that various other changes and modification may be effected therein by one skilled in the art without departing from the scope or spirit of the disclosure.

What is claimed is:

1. An electrosurgical system comprising:
    an electrosurgical generator including:
        an output stage, having a non-resonant inverter, configured to generate electrosurgical energy at a plurality of radio frequencies;
        a plurality of sensors configured to sense a voltage waveform and a current waveform of the electrosurgical energy; and
        a controller coupled to the output stage and the plurality of sensors; and
    an instrument coupled to the electrosurgical generator and configured to supply the electrosurgical energy to tissue,
    wherein the controller is further configured to calculate at least one parasitic parameter based on the electrosurgical energy at the plurality of radio frequencies and control the output stage to adjust an amplitude of the electrosurgical energy based on the at least one parasitic parameter.

2. The electrosurgical system according to claim 1, further comprising a cable serially coupling the instrument to the electrosurgical generator.

3. The electrosurgical system according to claim 2, wherein the at least one parasitic parameter includes an inductive impedance and a capacitive impedance of the cable.

4. The electrosurgical system according to claim 3, wherein the at least one parasitic parameter further includes a capacitive impedance of the instrument.

5. The electrosurgical system according to claim 4, wherein the capacitive impedance of the cable and the capacitive impedance of the instrument are connected in parallel.

6. The electrosurgical system according to claim 2, wherein the controller is further configured to calculate an output impedance at each of the plurality of radio frequencies based on the sensed voltage and current waveforms.

7. The electrosurgical system according to claim 6, wherein the controller is further configured to calculate the at least one parasitic parameter based on the output impedance at each of the plurality of radio frequencies.

8. The electrosurgical system according to claim 1, wherein a number of the plurality of radio frequencies is based on a number of the at least one parasitic parameter.

9. The electrosurgical system according to claim 1, wherein the controller calculates the at least one parasitic parameter before or during transmission of the electrosurgical energy to the instrument.

* * * * *